United States Patent
Alain (10) Patent No.: US 8,226,688 B2
(45) Date of Patent: Jul. 24, 2012

(54) DEVICE TO PROTECT ADJACENT STAGES OF A SPINAL SEGMENT

(75) Inventor: Tornier Alain, Saint-Ismier (FR)

(73) Assignee: Clariance, Dainville (FR)

( * ) Notice: Subject to any disclaimer, the term of this patent is extended or adjusted under 35 U.S.C. 154(b) by 153 days.

(21) Appl. No.: 12/813,850

(22) Filed: Jun. 11, 2010

(65) Prior Publication Data

US 2010/0318133 A1  Dec. 16, 2010

Related U.S. Application Data (60) Provisional application No. 61/186,536, filed on Jun. 12, 2009.

(30) Foreign Application Priority Data

Jun. 11, 2009  (FR) ..................................... 09 02829

(51) Int. Cl.
*A61B 17/70* (2006.01)
(52) U.S. Cl. ......................... 606/248; 606/246; 606/249
(58) Field of Classification Search .......... 606/246–253; 623/17.11–17.16
See application file for complete search history.

(56) References Cited

U.S. PATENT DOCUMENTS 7,862,591 B2 * 1/2011 Dewey et al. .................. 606/248
2008/0281361 A1 11/2008 Vittur et al.

FOREIGN PATENT DOCUMENTS

WO 2007/052975 A 5/2007

OTHER PUBLICATIONS

French Search Report in Corresponding Application No. FA 723472/FR 0902829 Dated Nov. 17, 2009.

* cited by examiner

*Primary Examiner* — Eduardo C Robert
*Assistant Examiner* — Christina Negrelli
(74) *Attorney, Agent, or Firm* — Young & Thompson (57) ABSTRACT

The device for protecting adjacent stages Vc of a spinal segment Sr of a vertebral column previously instrumented by an osteosynthesis device (1) is constituted of fixation elements (110) formed of connectors (111) immobilized in translation and in rotation on the corresponding connection rod (4) of osteosynthesis device (1), a support block (130; 180) in which is housed the spinous process Ve of superjacent vertebra Vc found just above the instrumented spinal segment Sr and at least one ligament (150, 170, 190) allowing spinous process Ve of superjacent vertebra Vc to be joined to support block (130; 180) and the support block (130; 180) to be joined to connectors (111).

14 Claims, 9 Drawing Sheets

DEVICE TO PROTECT ADJACENT STAGES OF A SPINAL SEGMENT

The present invention relates to a device to protect adjacent stages of a spinal segment of a vertebral column instrumented by an osteosynthesis device.

In the case of fusion of several vertebrae, it is observed that the capacity for movement of the vertebrae is more or less eliminated. This loss of mobility mainly depends on the number of vertebrae immobilized by the spinal osteosynthesis device. Due to this loss of mobility, the patient will seek to compensate for the loss by overactivating the adjacent stages.

Regarding the lumbar part of the vertebral column, that is very mobile compared to the thoracic part, the search for mobility preferentially will be done on the superjacent or superior stages due to the significant leverage that the trunk represents.

It will be observed that this search for mobility is focused on a single vertebral stage and mainly on the stage found immediately above the instrumented spinal segment, leading in the medium term to deterioration of said vertebral stage.

Devices to protect the adjacent stages of an instrumented spinal segment are known that are constituted of, for example, flexible rods, articulated or other, fixed through pedicle screws anchored in the vertebra of the superjacent stage.

It is noted that these protection devices are no more or less than an extension of the posterior fixation performed by the spinal osteosynthesis device, almost permanently blocking the superjacent stage to be protected.

The object of the protection device according to the present invention is to allow the patient, in search of additional mobility on the superjacent stages of an instrumented spinal segment, to be able to rehabilitate several vertebrae, not only the vertebra found just above, by limiting amplitudes, especially in flexion-extension, that are the principal movements at the lumbar part stage of the vertebral column.

The protection device according to the present invention is in addition to the spinal osteosynthesis device fusing the instrumented spinal segment in order to carry out retention limiting the extension of the flexion of the superjacent vertebra.

The protection device according to the present invention retains the surrounding tissues in a non-traumatic manner. The protection device according to the present invention may also be utilized in case of excision of spinous processes of vertebral stages of the instrumented spinal segment.

The protection device according to the present invention comprises connection rods constituted of connectors immobilized in translation and in rotation on the corresponding connection rod, a support block in which is housed spinous process Ve of superjacent vertebra Vc found just above the instrumented spinal segment Sr and upper and lower ligaments, allowing, first, spinous process Ve of superjacent vertebra Vc to be joined to the support block and, second, the support block to be joined to the connectors.

The protection device according to the present invention comprises, for each connector, a lateral housing with an inner cylindrical profile that is open to the outside to enable the introduction and snap insertion of the corresponding connection rod, tightening means allowing the immobilization in translation and in rotation of each connector on the corresponding connection rod and grooves cooperating with blocking means for holding the upper and lower ligaments.

The protection device according to the present invention comprises, for each connector at the level of each groove outlet, an indentation intended to receive the support block.

The protection device according to the present invention comprises grooves that lead to the inside of a cavity arranged at the center of the connector, inside of which a cam allowing tightening of upper and lower ligaments cooperates along a direction perpendicular to that of said grooves.

The protection device according to the present invention comprises a support block that is made of an elastic material so as to be able to deform under outside pressure and more particularly under the pressure of the superjacent vertebra Vc found just above the instrumented spinal segment Sr.

The protection device according to the present invention comprises a support block that presents an inverted U-shaped profile comprising an upper bridge extending by support legs in which grooves are arranged to respectively allow the placement and holding of upper and lower ligaments.

The protection device according to the present invention comprises a first groove that is open towards the outside and arranged on the side of each support leg of the support block.

The protection device according to the present invention comprises a second groove that is open towards the outside and arranged in a continuous manner in the thickness of each support leg and upper bridge of the support block.

The protection device according to the present invention comprises an upper bridge that comprises a housing allowing spinous process Ve of superjacent vertebra Vc to be placed.

The protection device according to the present invention comprises a groove that passes below the housing arranged in the bridge.

The protection device according to the present invention comprises a second groove comprising an opening towards the outside made along a direction that is perpendicular to that provided for the first groove.

The protection device according to the present invention comprises a connector that comprises a lateral housing with an inner cylindrical profile allowing the introduction and snap insertion of the corresponding connection rod, a threaded bore leading to the inside of said housing and cooperating with a tightening screw allowing the immobilization in translation and in rotation of each fixation element, a groove with an oblong profile traversing the connector and allowing passage of the synthetic ligament, a cavity arranged in the center of the connector, inside of which a threaded bore appears, along a direction perpendicular to that of the groove, allowing, first, the introduction of a locking key inside said cavity and, second, the tightening of a counter nut allowing said locking key to be immobilized in rotation.

The protection device according to the present invention comprises a locking key that is constituted of a cylindrical pin comprising, first, a head equipped with an indentation and, second, opposite said head and along a vertical and central axis, a groove separating said cylindrical pin into two distinct parts, said groove being provided to be traversed by the synthetic ligament when the locking key is placed inside the cavity of the connector.

The protection device according to the present invention comprises a counter nut that comprises a central through-bore for the passage of a tool so that the latter may be housed inside the indentation of the locking key in view of leading said locking key in rotation inside the cavity of the corresponding connector for winding the ligament around the cylindrical pin.

The protection device according to the present invention comprises a support block that presents an inverted U-shaped profile comprising an upper bridge connected by two support legs arranged to pass on both sides of spinous process Ve of vertebra Vb of instrumented spinal segment Sr, said upper bridge comprising a housing cooperating with spinous process Ve of superjacent vertebra Vc, while said support legs comprise, first, on the outer inverted U-shaped profile, a groove open towards the outside allowing the placement, retention and guiding of the synthetic ligament and, second, at each free end, a base extended by a flange equipped with a peripheral recess allowing the support block to be held inside a complementarily-shaped housing made inside each connector.

The protection device according to the present invention comprises a groove that traverses each base and the flange such that the latter is found, when the block is assembled in the connectors, in the extension of the groove.

The description that will follow with regard to the attached drawings, given by way of non-limiting examples, will allow the invention, the characteristics that it presents and the advantages that it is likely to procure to be better understood.

Figure 1:
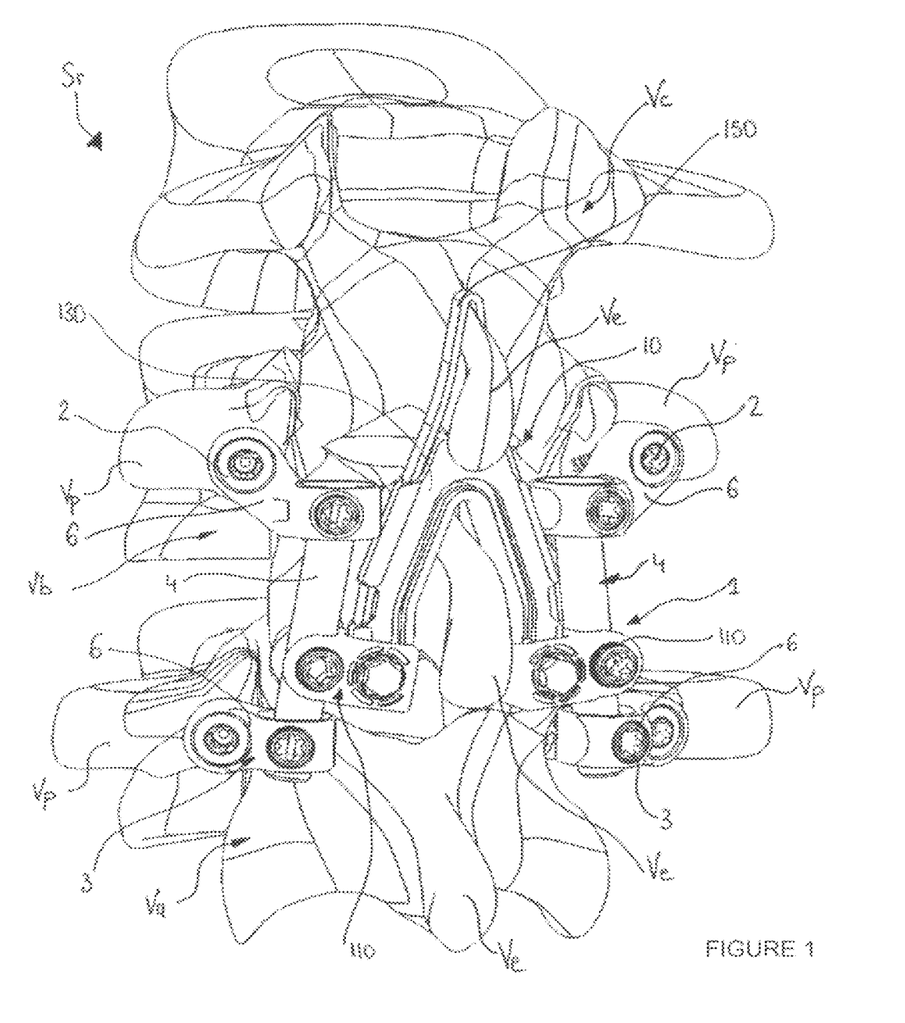
FIG. 1 is a perspective view illustrating the protection device according to the present invention assembled as an addition, for example on a spinal osteosynthesis device with a connection rod known in itself allowing fusion of a spinal segment of a vertebral column.
Figure 2:
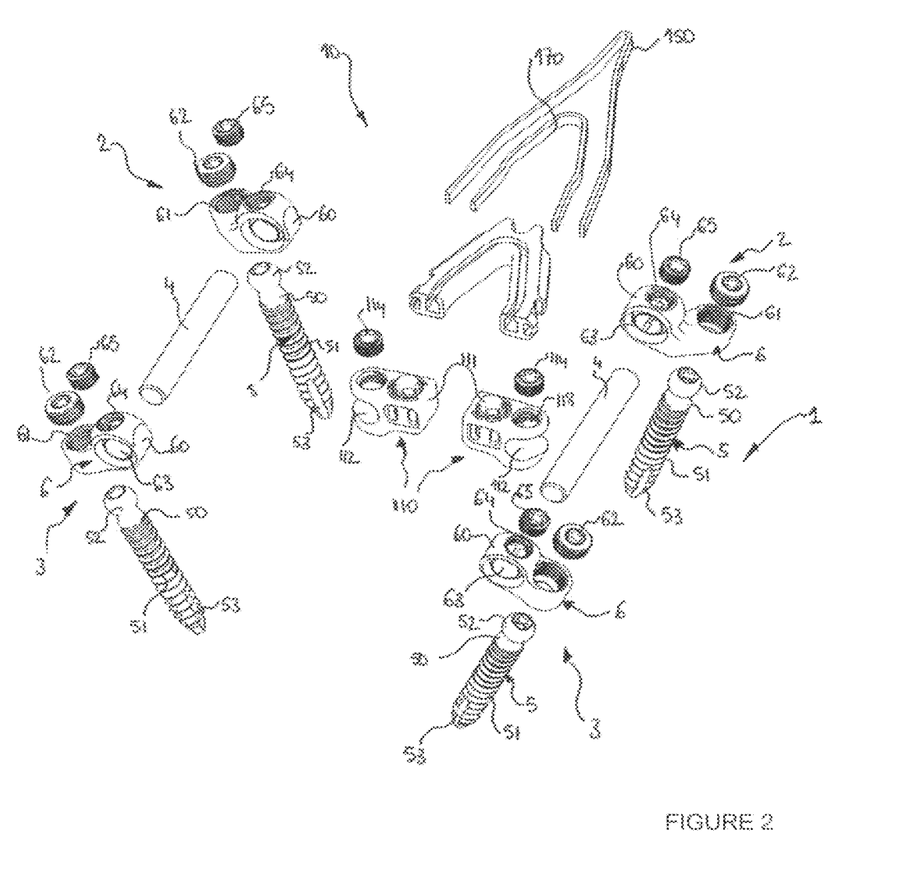
FIG. 2 is a blow-up perspective view showing the different elements constituting the protection device and the spinal osteosynthesis device according to the present invention.

FIGS. 1 and 2 represent an instrumented spinal segment Sr of a vertebral column wherein certain vertebrae, more particularly lumbar vertebrae Va, Vb are interconnected for example by a spinal osteosynthesis device 1 and by a protection device 10.

By way of non-limiting example, the spinal osteosynthesis device 1 is constituted of anchoring elements 2, 3 being respectively fixed in pedicles Vp of lumbar vertebrae Va, Vb of spinal segment Sr to be instrumented.

The spinal osteosynthesis device 1 comprises longitudinal connection or connection rod elements 4 disposed on both sides of spinous processes Ve of lumbar vertebrae Va, Vb in order to connect each first anchoring element 2 with the corresponding second anchoring element 3.

The first and second anchoring elements 2, 3 each comprise a pedicle screw 5 and a connection connector 6 known in itself.

Each pedicle screw 5 is constituted of a longitudinal body 50 presenting a threaded part 51 intended for the anchoring of said screw in the osseous body of pedicles Vp of each lumbar vertebra Va, Vb of spinal segment Sr to be instrumented.

Longitudinal body 50 comprises, in the extension of the threaded part 51, a head 52 with a spherical profile allowing the connection connector 6 to be placed and angularly adjusted.

Also, the pedicle screws 5 may be cannulated with the lateral openings 53 allowing biological cement intended to improve the anchoring in each lumbar vertebrae Va, Vb of spinal segment Sr to be instrumented to be injected.

Each connection connector 6 is constituted of a body 60 presenting a first bore 61 for housing the spherical head 52 of the corresponding pedicle screw 5. The connection connector 6 is immobilized on the pedicle screw 5 in an angular position determined by means of a clinch nut 62 cooperating with the upper threaded part of bore 61 in order to closely abut against spherical head 52.

Body 60 of each connection connector 6 comprises, along a direction perpendicular to that of bore 61 and laterally offset, another bore 63 allowing the corresponding connection rod 4 interconnecting said connection connectors 6 to be placed.

Body 60 comprises, along a direction parallel to that of bore 61, a threaded bore 64 cooperating with a tightening screw 65 ensuring the immobilization in translation and in rotation of connection rod 4 with relation to said connector 6.

Figure 3:
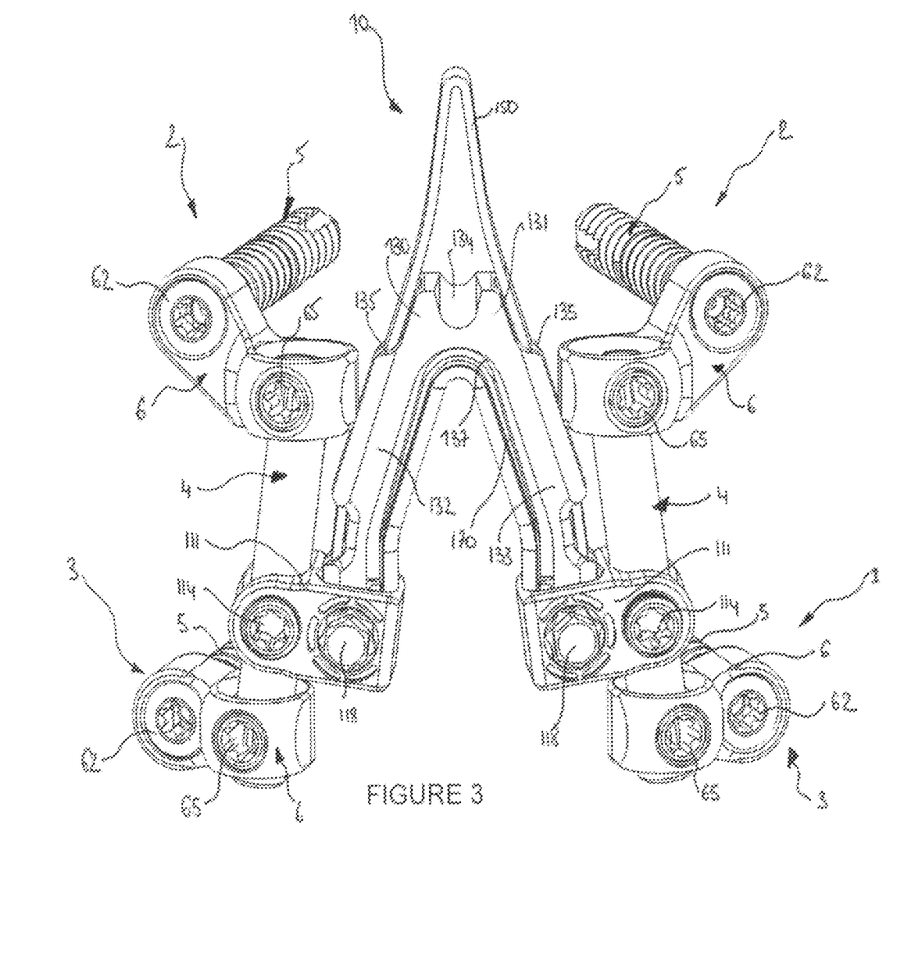
FIG. 3 is a perspective view representing the protection device according to the present invention assembled on a spinal osteosynthesis device known in itself.
Figure 4:
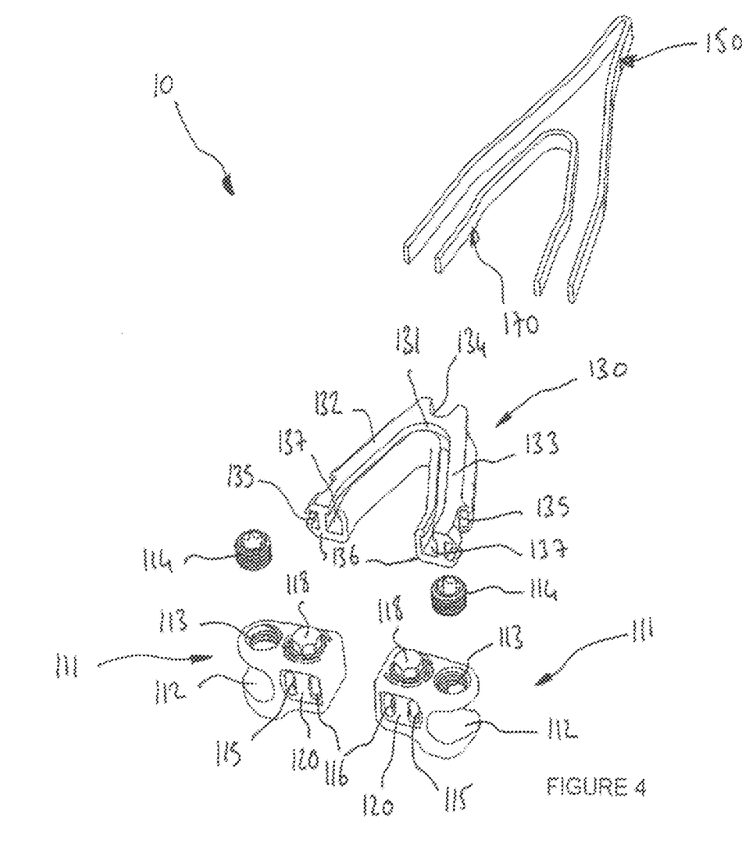
FIG. 4 is a blow-up perspective view illustrating the different elements constituting the protection device according to the present invention.
Figure 5:
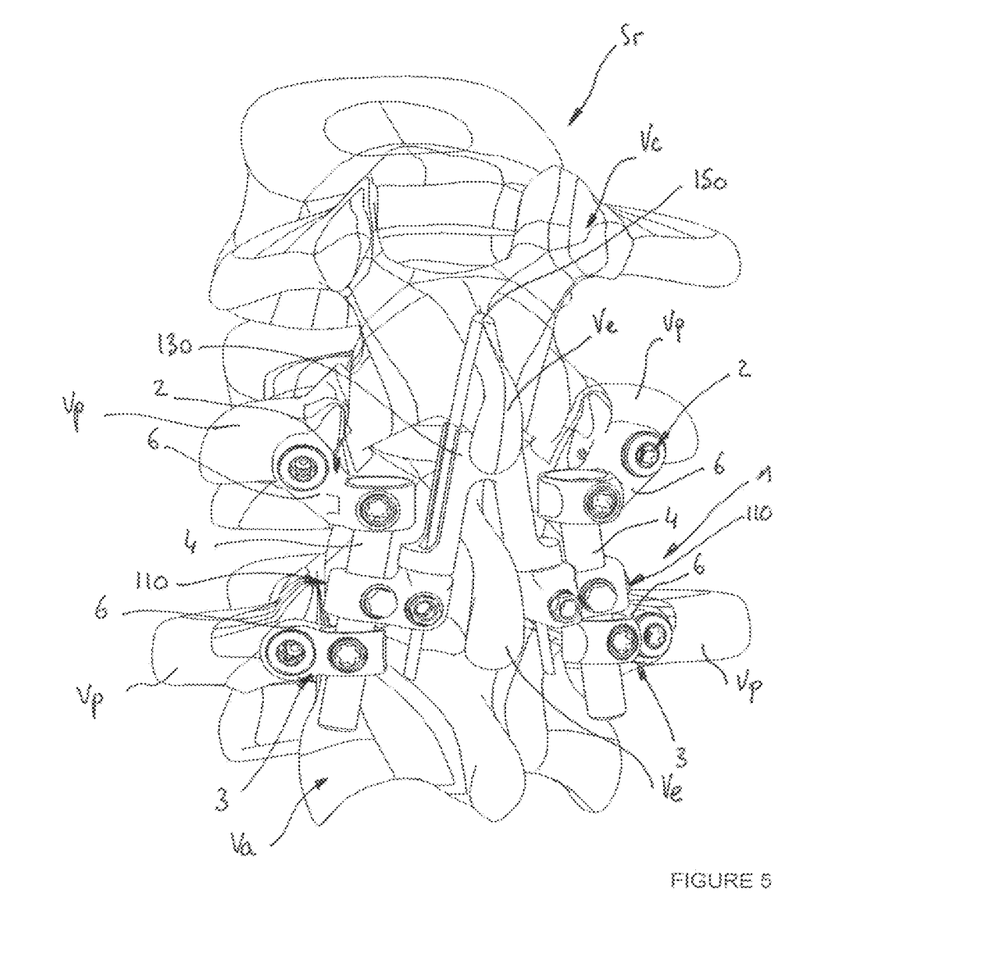
FIG. 5 is a perspective view showing a variation of the protection device according to the present invention.
Figure 6:
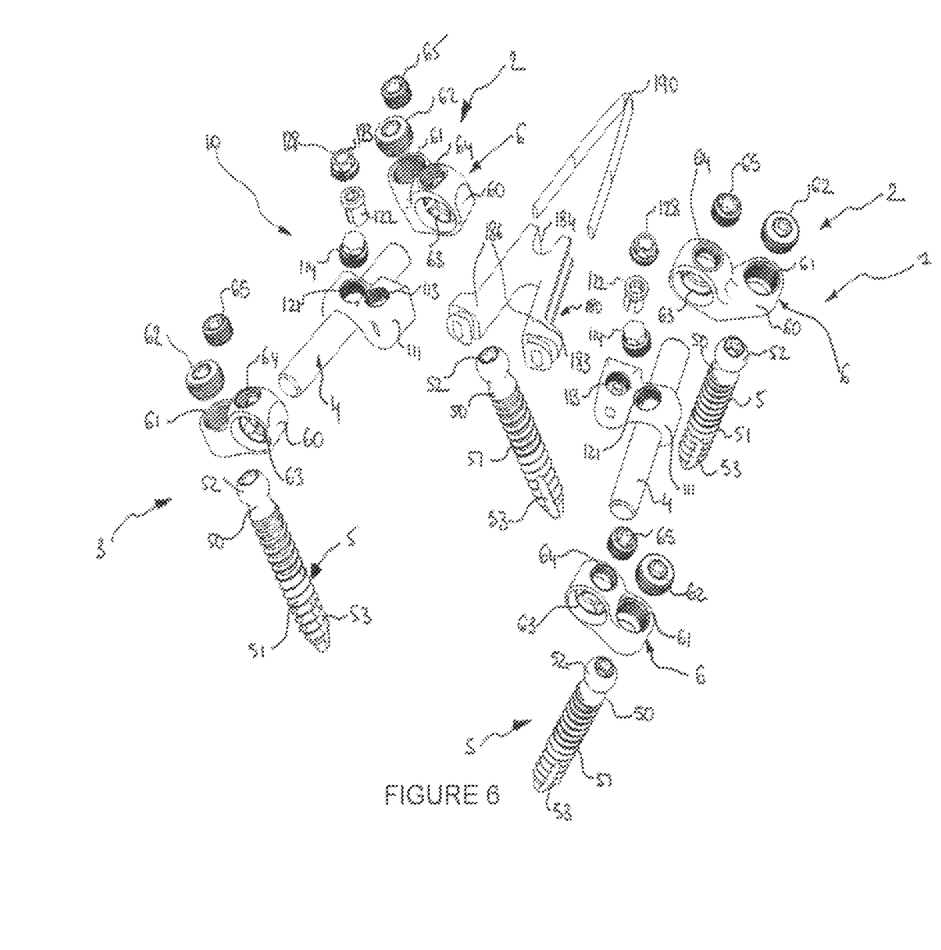
FIG. 6 is a blow-up perspective view showing the different elements constituting the protection device according to FIG. 5 and the spinal osteosynthesis device according to the present invention.
Figure 7:
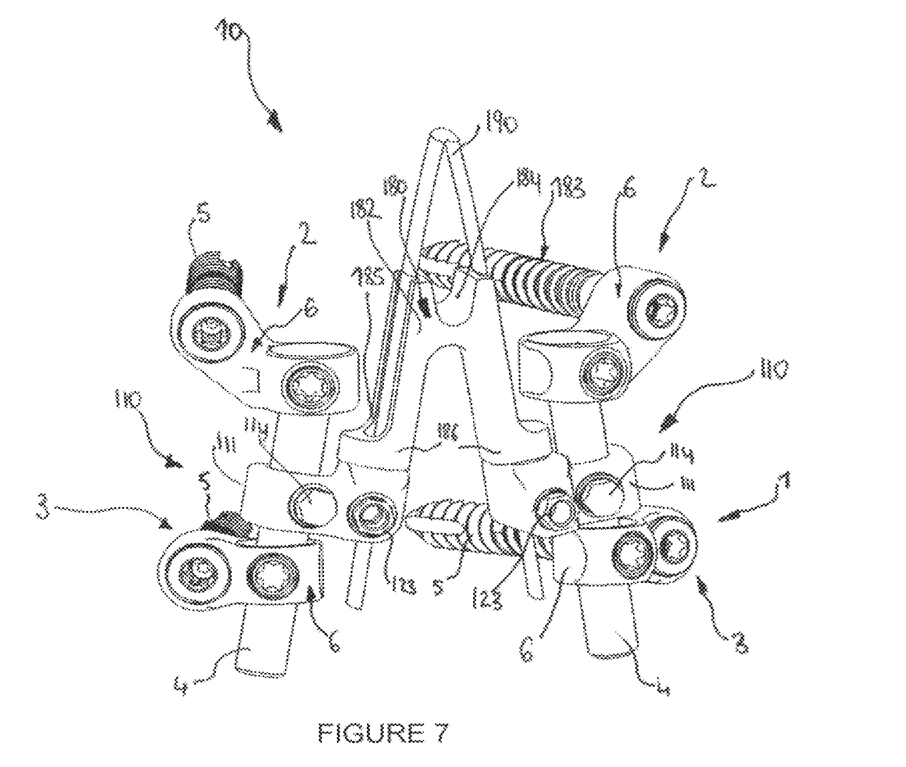
FIG. 7 is a perspective view representing the protection device from FIG. 5 assembled on a spinal osteosynthesis device known in itself.

FIGS. 3 and 4 show protection device 10 according to the present invention that is provided to be set out and fixed on any spinal osteosynthesis device 1 whatsoever as soon as the latter comprises, on both sides of spinous processes Ve of instrumented vertebrae Va, Vb, connection rods 4.

The protection device 10 is constituted of fixation elements 110 positioned and fixed on each of connection rods 4 of the spinal osteosynthesis device 1, a support block 130 supported by fixation elements 110 and synthetic ligaments 150, 170 allowing said protection device 10 to be joined to the spinous process Ve of the superjacent vertebra Vc found just above the spinal segment Sr instrumented by the spinal osteosynthesis device 1.

The fixation element 10 is constituted of a connector 111 comprising a lateral housing 112 with an inner cylindrical profile open towards the outside to allow the introduction and snap insertion of the corresponding connection rod 4 of the spinal osteosynthesis device 1.

The connector 111 is pierced above the lateral housing 112 by a threaded bore 113 leading inside said housing and cooperating with a tightening screw 114 allowing the immobilization in translation and in rotation of each fixation element 110 on the corresponding connection rod 4.

Parallel to the longitudinal axis of the lateral housing 112, the connector 111 comprises two grooves 115, 116 with an oblong profile traversing connector 111 and allowing passage of synthetic ligaments 150, 170.

Grooves 115, 116 lead to the inside of a cavity 117 arranged at the center of connector 111, inside of which a cam 118 allowing tightening of synthetic ligaments 150, 170 cooperates along a direction perpendicular to that of the grooves.

Connector 111 comprises, at the level of each groove 115, 116 outlet, an indentation 120 intended to receive the support block 130 and whose inner profile is similar to the external profile of said support block.

The support block 130 of the protection device 10 is made of an elastic material so as to be able to deform under outside pressure and more particularly under the pressure of the superjacent vertebra Vc.

The support block 130 presents an inverted U-shaped profile comprising an upper bridge 131 connected by two support legs 132, 133 arranged so as to pass on both sides of the spinous process Ve of vertebra Vb of the instrumented spinal segment Sr.

The upper bridge 131 of support block 130 comprises a housing 134 cooperating with the spinous process Ve of the superjacent vertebra Vc.

On the inverted U-shaped profile, support legs 132, 133 of support block 130 comprise a first groove 135 open towards the outside and allowing the placement, retention and guiding of first synthetic ligament 150.

The first groove 135 is arranged in the thickness and on the side of each support leg 132, 133 of support block 130, so that said groove 135 appears at the level of bases 136 of said support legs 132, 133.

On the inverted U-shaped profile, support legs 132, 133 and upper bridge 131 of support block 130 comprise a second groove 137 open towards the outside and allowing the placement, retention and guiding of second synthetic ligament 170.

The second groove 137 is arranged in a continuous manner in the thickness of each support leg 132, 133 of the upper bridge 131 of the support block 130 so that said groove 137 passes below the housing 134 to appear at the level of bases 136 of said support legs 132, 133.

The opening towards the outside of the second groove 137 is done along a direction that is perpendicular to that provided for the second groove 135.

Each opening towards the outside of each groove 135, 137 presents a dimension that is less than the inner dimension of said grooves so as to retain the synthetic ligament 150, 170 inside the corresponding groove 135, 137.

The protection device 10 comprises two synthetic ligaments 150, 170 allowing the inverted U-shaped support block 130 to be maintained on the fixation elements 110 fixed on each of connection rods 4 of the spinal osteosynthesis device 1.

The first ligament 150 housed inside the first groove 135 of the support block 130 is provided to pass above spinous process Ve of superjacent vertebra Vc found just above the instrumented spinal segment Sr so that said spinous process Ve of superjacent vertebra Vc is maintained inside housing 134 of said block, while the two free ends of said first ligament 150 respectively traverse fixation elements 110 fixed on each connection rod 4 through groove 115 and cam 118.

The second ligament 170 housed inside the second groove 137 of support block 130 is provided to pass below spinous process Ve of superjacent vertebra Vc and above spinous process Ve of vertebra Vb of the instrumented spinal segment Sr, while the two free ends of said second ligament 170 respectively traverse fixation elements 110 fixed on each connection rod 4 through groove 116 and cam 118.

The operation of protection device 10 according to the present invention can be easily understood from the previous description.

In fact, after fusing vertebrae Va and Vb of spinal segment Sr by the spinal osteosynthesis device 1, the surgeon places and fixes protection device 10 of the superjacent stage formed by the superjacent vertebra Vc.

The surgeon carries out the placement, on one of the connection rods 4 of spinal osteosynthesis device 1, of a fixation element 110 formed by a first connector 111 that is previously connected to the support block 130 through two synthetic ligaments 150, 170 placed in the corresponding grooves 135, 137 of leg 132.

In fact, one of the ends of the two synthetic ligaments 150, 170 is held blocked in the first connector 111 through cam 118. The support block 130 abuts against the first connector 111 so that, for example, the support base 136 of leg 132 is housed inside indentation 120 of said connector.

The surgeon positions, by pivoting the first connector 111 around the connection rod 4, the support block 130 equipped with two synthetic ligaments 150, 170 held in the first connector 111 between vertebra Vb of spinal segment Sr instrumented by the spinal osteosynthesis device 1 and the superjacent vertebra Vc so that spinous process Ve of said superjacent vertebra Vc is placed inside housing 134 arranged in the upper bridge 131 of said support block 130.

Then, the surgeon disposes the upper ligament 150 around the spinous process Ve of superjacent vertebra Vc and introduces it into groove 135 arranged in the other leg 133 of the support block 130. The surgeon tightens the upper ligament 150 and, by using the tightening screw 114, immobilizes in translation and in rotation the first connector 111 on the connection rod 4 of the spinal osteosynthesis device 1.

The surgeon introduces the other free ends of the upper and lower ligaments 150 and 170 into the corresponding grooves 115 and 116 of another fixation element 110 formed by a second connector 111 in order to traverse the latter.

While maintaining tension on upper and lower ligaments 150 and 170, the surgeon brings the second connector 111 against the support base 136 of the second leg 133 of the support block 130, positions said connector 111 on the other connection rod 4 of the spinal osteosynthesis device 1 and immobilizes it in rotation and in translation through tightening screw 114.

While maintaining tension on upper and lower ligaments 150 and 170, the surgeon tightens the latter in the second connector 111 by means of cam 118.

Lastly, the surgeon cuts the ends of the upper and lower ligaments 150 and 170 exceeding the first and second connectors 111 of protection device 10.

FIGS. 5 to 9 show a variation of protection device 10 according to the present invention that is provided to be set out and fixed on any spinal osteosynthesis device 1 whatsoever as soon as the latter comprises, on both sides of spinous processes Ve of instrumented vertebrae Va, Vb, connection rods 4.

The spinal osteosynthesis device 1 on which the variation of the protection device 10 is assembled and fixed is similar to that described previously in FIGS. 1 to 4 of the present invention, but is mainly distinguished in that it comprises a support block 180 arranged to receive only one synthetic ligament 190.

The protection device 10 is constituted of fixation elements 110 positioned and fixed on each of connection rods 4 of the spinal osteosynthesis device 1, a support block 180 supported by fixation elements 110 and a synthetic ligament 190 allowing said protection device 10 to be joined to the spinous process Ve of the superjacent vertebra Vc found just above the spinal segment Sr instrumented by the spinal osteosynthesis device 1.

The fixation element 110 is constituted of a connector 111 comprising a lateral housing 112 with an inner cylindrical profile open towards the outside to allow the introduction and snap insertion of the corresponding connection rod 4 of the spinal osteosynthesis device 1.

The connector 111 is pierced above the lateral housing 112 by a threaded bore 113 leading inside said housing and cooperating with a tightening screw 114 allowing the immobilization in translation and in rotation of each fixation element 110 on the corresponding connection rod 4.

Parallel to the longitudinal axis of the lateral housing 112, the connector 111 comprises a groove 119 with an oblong profile traversing the connector 111 and allowing the passage of synthetic ligament 190. Groove 119 leads to the inside of a cavity 117 arranged in the center of connector 111 and inside of which appears, along a direction perpendicular to that of the groove, a threaded bore 121 allowing, first, a locking key 122 to be introduced inside cavity 117 and, second, a counter nut 123 to be tightened.

Figure 8:
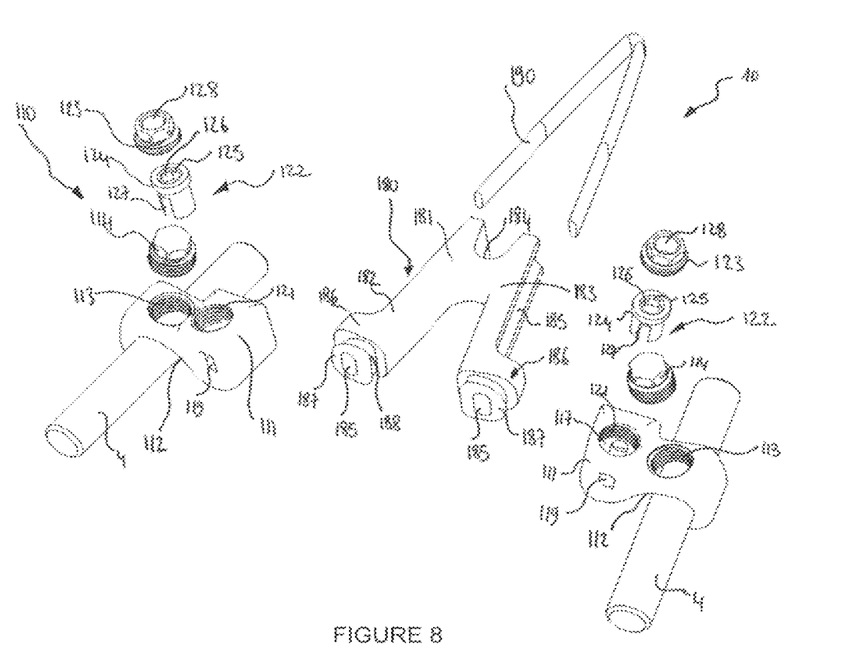
FIGS. 8 and 9 are blow-up perspective views illustrating the different elements constituting the protection device from FIG. 5 according to the present invention.
Figure 9:
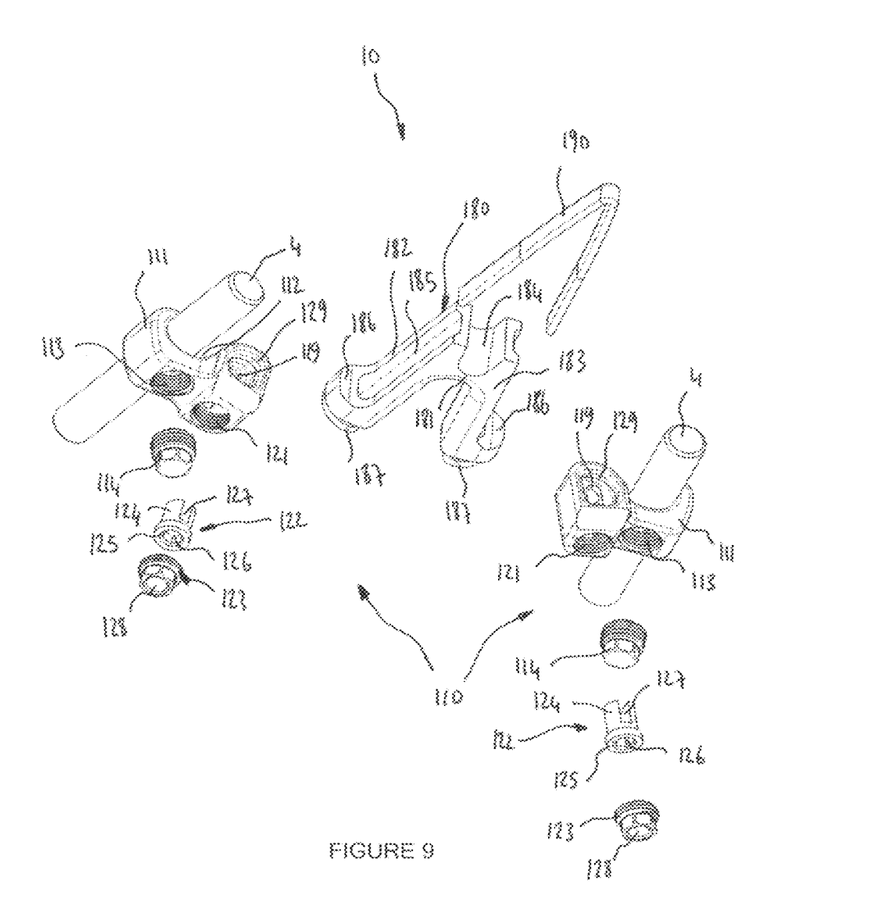

The locking key 122 is constituted of a cylindrical pin 124 comprising, first, a head 125 equipped with an indentation 126 and, second, opposite said head 125 and along a vertical and central axis, a groove 127 separating said cylindrical pin 124 into two distinct parts.

Groove 127 is provided to be traversed by synthetic ligament 190 when locking key 122 is placed inside cavity 117 of connector 111.

After adjusting the tension of and immobilizing synthetic ligament 190, locking key 122 is immobilized inside cavity 117 of each connector 111 through the counter nut 123 that abuts against head 125 after tightening.

The counter nut 123 comprises a central through-bore 128 allowing the passage of a tool so that the latter may be housed inside indentation 126 of locking key 122. The tool allows the locking key 122 to be driven in rotation inside cavity 117 of the corresponding connector 111 allowing, after tensioning of ligament 190, the ligament to be wound around the cylindrical pin 124 of said locking key 122.

Each connector 111 comprises, at the level of groove 119, an indentation 129 intended to receive each base 186 of support block 180 and whose inner profile is similar to the external profile of said support block.

The support block 180 of the protection device 10 is made of an elastic material so as to be able to deform under outside pressure and more particularly under the pressure of the superjacent vertebra Vc.

The support block 180 presents an inverted U-shaped profile comprising an upper bridge 181 connected by two support legs 182, 183 arranged so as to pass on both sides of the spinous process Ve of vertebra Vb of the instrumented spinal segment Sr.

The upper bridge 181 of support block 180 comprises a housing 184 cooperating with the spinous process Ve of the superjacent vertebra Vc.

On the inverted U-shaped external profile, support legs 182, 183 of support block 180 comprise a first groove 185 open towards the outside and allowing the placement, retention and guiding of synthetic ligament 190.

Each base 186 is extended by a flange 187 equipped with a peripheral recess 188 allowing the support block 180 to be held inside a complementarily-shaped housing made inside each connector 111.

Groove 185 traverses each base 186 and flange 187 so that the flange is found, during assembly of block 180 in connectors 111, in the extension of groove 119 of the connectors so that each connector is traversed by the free end of ligament 190.

The operation of protection device 10 comprising a single ligament 190 can be easily understood from the previous description.

In fact, after fusing vertebrae Va and Vb of spinal segment Sr by the spinal osteosynthesis device 1, the surgeon places and fixes protection device 10 of the superjacent stage formed by the superjacent vertebra Vc.

On one of the connection rods 4 of the spinal osteosynthesis device 1, the surgeon places a fixation element 110 formed by a first connector 111 previously connected to the support block 180 and to the synthetic ligament 190.

In fact, flange 187 of base 186 of support block 180 is overmolded in housing 129 provided for this purpose of connector 111, while one of the free ends of ligament 190 is blocked in said connector by means of the locking key 122 and the counter nut 123.

The surgeon positions, by pivoting the first connector 111 around the connection rod 4, the support block 180 equipped with the synthetic ligaments 190 held in the first connector 111 between vertebra Vb of spinal segment Sr instrumented by the spinal osteosynthesis device 1 and the superjacent vertebra Vc so that spinous process Ve of said superjacent vertebra Vc is placed inside housing 184 arranged in the upper bridge 181 of said support block 180.

Then, the surgeon disposes ligament 190 around the spinous process Ve of superjacent vertebra Vc and introduces it into groove 185 arranged in legs 182, 183 of the support block 180. By using the tightening screw 114, the surgeon immobilizes in translation and in rotation the first connector 111 on the first connection rod 4 of the spinal osteosynthesis device 1.

The surgeon introduces the other free end of ligament 190 in the corresponding groove 119 of another fixation element 110 formed by a second connector 111 in order to traverse the connector. The connector 111 is assembled on the other connection rod 4 of the spinal osteosynthesis device 1 in order to traverse the device.

The surgeon slips the block 180 and connector 110 assembly between spinous processes Ve and then positions, by pivoting, the first connector 111 around the connection rod 4 and then the second connector and then tightens the two screws 114.

The surgeon first carries out tensioning of ligament 190 and second carries out the immobilization in rotation and in translation of second connector 111 through tightening screw 114 on the other connection rod 4 of the spinal osteosynthesis device 1.

While maintaining the tension of ligament 190, the surgeon blocks the ligament by driving locking key 122 in rotation inside cavity 117 so that ligament 190 is wound around cylindrical pin 124.

The surgeon holds locking key 122 in position while it is blocked in rotation by the counter nut 123.

Lastly, the surgeon cuts the ends of the ligament 190 exceeding the first and second connectors 111 of protection device 10.

In addition, it must be understood that the previous description was only given by way of example and that it in no way limits the field of the invention from which one will not depart by replacing the details of embodiment described by any other equivalent.

The invention claimed is:

1. A protection device for protecting adjacent stages Vc of a spinal segment Sr of a vertebral column instrumented by an osteosynthesis device (1) comprising connection rods (4), characterized in that the device is constituted of fixation elements (110) formed of connectors (111) immobilized in translation and in rotation on the corresponding connection rod (4) of osteosynthesis device (1), a support block (130; 180) presenting an inverted U-shaped profile and made of an elastic material in which is housed the spinous process Ve of superjacent vertebra Vc found just above the instrumented spinal segment Sr, at least one ligament (150, 170, 190) allowing spinous process Ve of superjacent vertebra Vc to be joined to support block (130; 180) and the support block (130; 180) to connectors (111) and a blocking means (118, 123) of the corresponding ligament (150, 170, 190), after tensioning, in connectors (111);
    wherein each connector (111) comprises a lateral housing (112) with an inner cylindrical profile that is open to the outside to enable the introduction and snap insertion of the corresponding connection rod (4), tightening means (113, 114) allowing the immobilization in translation and in rotation of each connector (111) on the corresponding connection rod (4) and grooves (115, 116) cooperating with the blocking means (118) for holding an upper (150) ligament and a lower (170) ligament, and the grooves (115, 116) lead to the inside of a cavity (117) arranged at the center of the connector (111) and inside of which cooperates, along a direction perpendicular to that of said grooves, a cam (118) allowing upper (150) and lower (170) ligaments to be tightened.

2. The protection device according to claim 1, characterized in that each connector (111) comprises, at the level of each groove (115, 116), an indentation (120) intended to receive the support block (130).

3. The protection device according to claim 1, characterized in that the support block (130) is made of an elastic material so as to be able to deform under outside pressure and more particularly under the pressure of the superjacent vertebra Vc found just above the instrumented spinal segment Sr.

4. The protection device according to claim 1, characterized in that the support block (130) presents an inverted U-shaped profile comprising an upper bridge (131) extending by support legs (132, 133) in which at least a first groove (135) and a second groove (137) are arranged to respectively allow the placement and holding of an upper (150) ligament and an lower (170) ligament.

5. The protection device according to claim 4, characterized in that the first groove (135) is open towards the outside and arranged on the side of each support leg (132, 133) of the support block (130).

6. The protection device according to claim 5, characterized in that the second groove (137) is open towards the outside and arranged in a continuous manner in a thickness of each support leg (132, 133) and of the upper bridge (131) of the support block (130), and characterized in that the opening towards the outside of the second groove (137) is made along a direction that is perpendicular to that provided for the first groove (135).

7. The protection device according to claim 4, characterized in that the upper bridge (131) comprises a housing (134) allowing spinous process Ve of superjacent vertebra Vc to be placed.

8. The protection device according to claim 7, characterized in that groove (137) passes below housing (134) arranged in the bridge (131).

9. The protection device according to claim 1, characterized in that the support block (180) presents an inverted U-shaped profile comprising an upper bridge (181) connected by two support legs (182, 183) arranged to pass on both sides of spinous process Ve of vertebra Vb of instrumented spinal segment Sr, said upper bridge (181) comprising a housing (184) cooperating with spinous process Ve of superjacent vertebra Vc, while said support legs (182, 183) comprise, first, on the outer inverted U-shaped profile, a groove (185) open towards the outside allowing the placement, retention and guiding of the synthetic ligament (190) and, second, at each free end, a base (186) extended by a flange (187) equipped with a peripheral recess (188) allowing the support block (180) to be held inside a complementarily-shaped housing (129) made inside each connector (111).

10. The protection device according to claim 9, characterized in that the groove (185) traverses each base (186) and flange (187) so that the flange is found, during assembly of block (180) in connectors (111), in the extension of the groove (119).

11. A protection device for protecting adjacent stages Vc of a spinal segment Sr of a vertebral column instrumented by an osteosynthesis device (1) comprising connection rods (4), characterized in that the device is constituted of fixation elements (110) formed of connectors (111) immobilized in translation and in rotation on the corresponding connection rod (4) of osteosynthesis device (1), a support block (130; 180) presenting an inverted U-shaped profile and made of an elastic material in which is housed the spinous process Ve of superjacent vertebra Vc found just above the instrumented spinal segment Sr, at least one ligament (150, 170, 190) allowing spinous process Ve of superjacent vertebra Vc to be joined to support block (130; 180) and the support block (130; 180) to connectors (111) and a blocking means (118, 123) of the corresponding ligament (150, 170, 190), after tensioning, in connectors (111), wherein the support block (130) presents an inverted U-shaped profile comprising an upper bridge (131) extending by support legs (132, 133) in which at least a first groove (135) and a second groove (137) are arranged to respectively allow the placement and holding of the upper (150) and lower (170) ligaments, and the second groove (137) is open towards the outside and arranged in a continuous manner in a thickness of each support leg (132, 133) and of the upper bridge (131) of the support block (130).

12. A protection device for protecting adjacent stages Vc of a spinal segment Sr of a vertebral column instrumented by an osteosynthesis device (1) comprising connection rods (4), characterized in that the device is constituted of fixation elements (110) formed of connectors (111) immobilized in translation and in rotation on the corresponding connection rod (4) of osteosynthesis device (1), a support block (130; 180) presenting an inverted U-shaped profile and made of an elastic material in which is housed the spinous process Ve of superjacent vertebra Vc found just above the instrumented spinal segment Sr, at least one ligament (150, 170, 190) allowing spinous process Ve of superjacent vertebra Vc to be joined to support block (130; 180) and the support block (130; 180) to connectors (111) and a blocking means (118, 123) of the corresponding ligament (150, 170, 190), after tensioning, in connectors (111), wherein each connector (111) comprises a lateral housing (112) with an inner cylindrical profile allowing the introduction and snap insertion of the corresponding connection rod (4), a threaded bore (113) leading to the inside of said housing and cooperating with a tightening screw (114) allowing the immobilization in translation and in rotation of each fixation element (110), a groove (119) with an oblong profile traversing the connector (111) and allowing passage of a synthetic ligament (190), a cavity (117) arranged in the center of the connector (111), inside of which a threaded bore (121) appears, along a direction perpendicular to that of the groove (119), allowing, first, the introduction of a locking key (122) inside said cavity (117) and, second, the tightening of a counter nut (123) allowing said locking key (122) to be immobilized in rotation.

13. The protection device according to claim 12, characterized in that the locking key (122) is constituted of a cylindrical pin (124) comprising, first, a head (125) equipped with an indentation (126) and, second, opposite said head (125) and along a vertical and central axis, a groove (127) separating said cylindrical pin (124) into two distinct parts, said groove (127) being provided to be traversed by the synthetic ligament (190) when the locking key (122) is placed inside the cavity (117) of the connector (111).

14. The protection device according to claim 13, characterized in that the counter nut (123) comprises a central through-bore (128) allowing the passage of a tool so that the latter may be housed inside the indentation (126) of locking key (122) in view of driving said locking key (122) in rotation inside cavity (117) of the corresponding connector (111) for winding the ligament (190) around the cylindrical pin (124).

* * * * *